United States Patent
Jahagirdar et al.

(10) Patent No.: US 8,974,825 B2
(45) Date of Patent: *Mar. 10, 2015

(54) PHARMACEUTICAL COMPOSITIONS FOR GASTROINTESTINAL DRUG DELIVERY

(75) Inventors: Harshal Anil Jahagirdar, Pune (IN); Rajesh Kulkarni, Pune (IN); Shirishkumar Kulkarni, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 768 days.

This patent is subject to a terminal disclaimer.

(21) Appl. No.: 12/144,894

(22) Filed: Jun. 24, 2008

(65) Prior Publication Data

US 2009/0011019 A1 Jan. 8, 2009

(30) Foreign Application Priority Data

Jul. 6, 2007 (IN) .............................. 969/KOL/2007

(51) Int. Cl.
*A61K 9/20* (2006.01)
*A61K 9/22* (2006.01)
*A61K 9/24* (2006.01)
*A61K 9/00* (2006.01)
*A61K 9/16* (2006.01)

(52) U.S. Cl.
CPC ............. *A61K 9/0095* (2013.01); *A61K 9/0065* (2013.01); *A61K 9/1611* (2013.01); *A61K 9/1623* (2013.01); *A61K 9/1635* (2013.01); *A61K 9/1641* (2013.01); *A61K 9/1652* (2013.01); *A61K 9/2009* (2013.01); *A61K 9/2013* (2013.01); *A61K 9/2018* (2013.01); *A61K 9/2027* (2013.01); *A61K 9/2031* (2013.01); *A61K 9/205* (2013.01); *A61K 9/2054* (2013.01); *A61K 9/2086* (2013.01); *A61K 9/209* (2013.01)
USPC ............................. 424/472; 424/464; 424/468

(58) Field of Classification Search
None
See application file for complete search history.

(56) References Cited

U.S. PATENT DOCUMENTS

| | | | | |
|---|---|---|---|---|
| 5,364,634 | A * | 11/1994 | Lew | 424/451 |
| 5,433,951 | A * | 7/1995 | Serajuddin et al. | 424/486 |
| 5,472,704 | A | 12/1995 | Santus et al. | |
| 5,900,247 | A | 5/1999 | Rault et al. | |
| 6,090,411 | A * | 7/2000 | Pillay et al. | 424/468 |
| 6,303,147 | B1 | 10/2001 | Gilis | |
| 6,306,789 | B1 | 10/2001 | Dettmar et al. | |
| 2003/0104052 | A1* | 6/2003 | Berner et al. | 424/468 |
| 2007/0154547 | A1* | 7/2007 | Flanner et al. | 424/468 |
| 2010/0330129 | A1* | 12/2010 | Viscomi et al. | 424/400 |

FOREIGN PATENT DOCUMENTS

| | | |
|---|---|---|
| GB | 2 042 888 | 10/1980 |
| WO | WO 2006/031420 | 3/2006 |

* cited by examiner

*Primary Examiner* — Susan Tran
(74) *Attorney, Agent, or Firm* — Merchant & Gould P.C.

(57) ABSTRACT

A novel pharmaceutical composition, which comprises a therapeutically effective amount of active principle(s) or a pharmaceutically acceptable salt or enantiomer or polymorph thereof, optionally one or more release controlling agent(s) and pharmaceutical acceptable excipient(s) thereof, wherein the composition is formulated to increase the residence time of the said pharmaceutical composition and/or active principle(s) in the gastrointestinal tract. A novel pharmaceutical composition comprising at least two entities wherein one entity is an immediate release/fast release and the other is controlled release. A pharmaceutical composition comprising at least two entities wherein one entity is an immediate release/fast release and the other is bioadhesive. A pharmaceutical composition comprising: at least two entities wherein one entity is controlled release and the other is bioadhesive All the three compositions are formulated to increase the residence time of active principle(s) in the gastrointestinal tract. A multilayered composition with active in a layer which provides immediate release or controlled release of active principles and layer providing increased residence time in the GI tract.

2 Claims, 1 Drawing Sheet

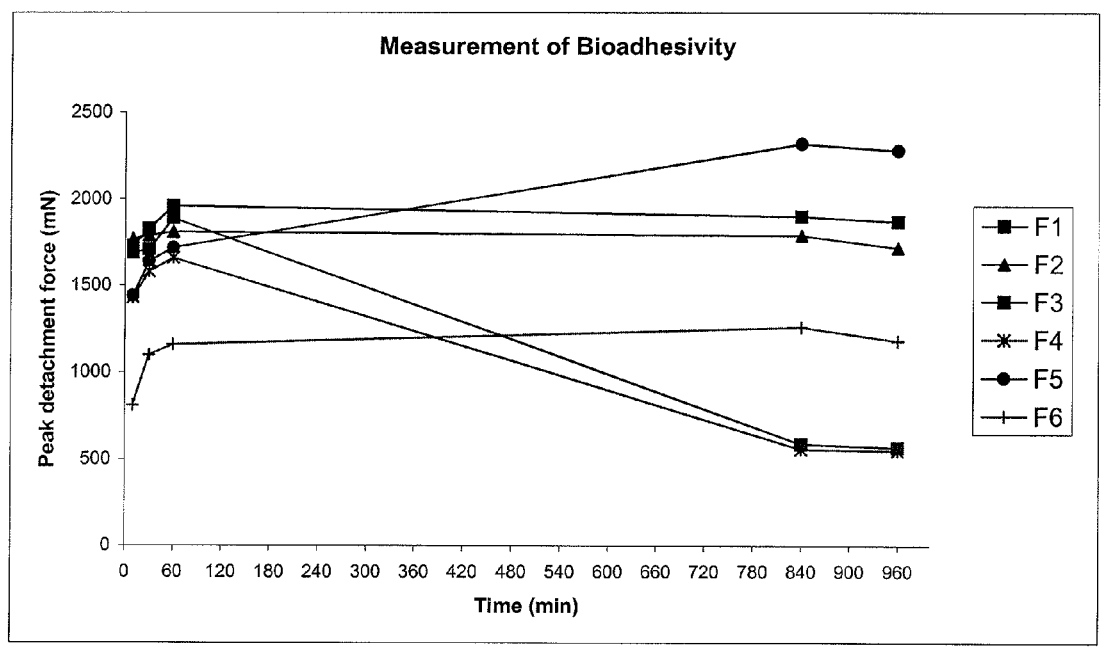

PHARMACEUTICAL COMPOSITIONS FOR GASTROINTESTINAL DRUG DELIVERY

FIELD OF THE INVENTION

The present invention relates to pharmaceutical formulations of active principle(s) for providing increased residence time in the gastrointestinal tract and the process of preparing them.

BACKGROUND OF THE INVENTION

A number of drugs act in the gastrointestinal tract. Oral drug administration is by far the most preferable route for taking medications. However, on oral administration, normal or pathological stomach voiding and intestinal peristaltic movements limit the time for which a drug-releasing dosage form remains in the gastrointestinal tract or at the required site of action. Specifically, during pathological conditions such as diarrhea, peristaltic movement of the GI Tract is increased. Therefore, GI transit time of dosage forms is lesser than normal. Hence conventional dosage forms have shorter residence time at the site of absorption or at required site of action and need to be dosed frequently in order to be therapeutically effective. A rational approach to solve this problem and to enhance bioavailability and improve pharmacokinetic and pharmacodynamic profiles is to retain the drug reservoir above its absorption area or the site of action, and to release the drug in a controlled manner, for a prolonged period of time. However, controlling the GI residence time is a challenge. We have surprisingly found that it is possible to extend the GI residence time of non-systemic locally acting drugs when administered in controlled release mucoadhesive dosage forms.

Drugs like (i) carbamazepine (an antiepileptic), furosemide (a diuretic), metoprolol (a beta blocker) and acyclovir (an antiviral) benefit from prolonged presence at or near the locus of absorption in terms of their bioavailability characteristics including drugs that act specifically on the gastrointestinal tract (e.g. 5-aminosalicylic acid) or which are absorbed most efficiently within the intestine or colon (e.g. peptides or proteins such as insulin, interferon, calcitonin, endorphins, human growth hormone, and various hormone growth factors).

Known bioadhesive solid dosage forms are described, for example, in GB-2,042,888 (Teijin). A slow release pharmaceutical preparation to be used adhering to the mucosa of the oral cavity (buccal) or nasal cavity comprising an active ingredient, 50 to 95% of a cellulose ether and 50 to 5% of a high molecular weight crosslinked polyacrylic acid (carboxyvinyl polymer, carbomer, carbopol).

U.S. Pat. No. 6,303,147 (Janssen) describes a bioadhesive pharmaceutical composition comprising a pharmaceutically effective amount of an active ingredient, from 80% to 98.8% (w/w) pre-gelatinized starch, and from 1% to 10% (w/w) of a hydrophilic matrix forming polymer, characterized in that the composition further comprises from 0.2% to 5% (w/w) alkaliC16-22 alkyl fumarate as a lubricant.

U.S. Pat. No. 6,306,789 (Reckitt Benckiser Healthcare) describes bioadhesive granules of carbomer and in particular to such granules containing pharmaceutical active agents suitable for sustained release into the gastrointestinal tract or for targeted delivery to the gastrointestinal mucosa.

U.S. Pat. No. 5,900,247 (Adir et compagnie) describes the bioadhesive films or patches characterized by the use: of a polymer (A) composed of one or a number of vinyl acetate/polyvinylpyrrolidone copolymers.

U.S. Pat. No. 5,472,704 (Recordati S. A.) describe composition characterized by plurality of small-size units capable of ensuring a gradual release of the active ingredient they contain the units being coated with a bioadhesive polymer layer. The composition makes it possible to keep the release controlling function separate from the function providing bioadhesion.

WO 2006/031420 (Spherics) describes bioadhesive formulation includes a multilayered core enveloped by a bioadhesive coating.

OBJECTS OF THE INVENTION

An object o the invention is to provide a novel pharmaceutical composition, which comprises a therapeutically effective amount of active principle(s) or a pharmaceutically acceptable salt or enantiomer or polymorph thereof, optionally one or more controlled release agent(s) and pharmaceutical acceptable excipient(s) thereof, wherein the composition is formulated to increase the residence time of the said pharmaceutical composition and/or active principle(s) in the gastrointestinal tract.

Another object of the invention is to provide a novel pharmaceutical composition comprising: at least two entities wherein one entity is an immediate release or fast release and the other is controlled release wherein the composition is formulated to increase the residence time of active principle(s) in the gastrointestinal tract.

Another object of the invention is to provide a novel pharmaceutical composition comprising: at least two entities wherein one entity is an immediate release or fast release and the other is bioadhesive wherein the composition is formulated to increase the residence time of active principle(s) in the gastrointestinal tract.

Another object of the invention is to provide a novel pharmaceutical composition comprising: at least two entities wherein one entity is controlled release and the other is bioadhesive wherein the composition is formulated to increase the residence time of active principle(s) in the gastrointestinal tract.

Another object of the invention is to provide a novel pharmaceutical composition in the form of a multilayer tablet comprising, a) at least one layer which comprises, a therapeutically effective amount of active principle(s) or a pharmaceutically acceptable salt or enantiomer or polymorph thereof, pharmaceutically acceptable excipient(s); wherein the said layer provides a immediate or fast release of active principle(s); and b) at least another layer which provides increased residence time of the dosage form in the gastrointestinal tract.

Another object of the invention is to provide a novel pharmaceutical composition in the form of a multilayer tablet comprising, a) at least one layer which comprises, a therapeutically effective amount of active principle(s) or a pharmaceutically acceptable salt or enantiomer or polymorph thereof, pharmaceutically acceptable excipient(s); wherein the said layer provides a controlled release of active principle(s); and b) at least another layer which provides increased residence time of the dosage form in the gastrointestinal tract.

Another object of the invention is to provide a novel pharmaceutical composition in the form of a multilayer tablet comprising, a) at least one layer which comprises, a therapeutically effective amount of active principle(s) or a pharmaceutically acceptable salt or enantiomer or polymorph thereof, pharmaceutically acceptable excipient(s); and b) at least one layer comprising another or same active principle(s)

wherein layer (b) provides increased residence time of the dosage form in the gastrointestinal tract.

Another object of the invention is to provide a novel pharmaceutical composition in the form of a multilayer tablet comprising, a) at least one layer which comprises, a therapeutically effective amount of active principle(s) or a pharmaceutically acceptable salt or enantiomer or polymorph thereof, pharmaceutically acceptable excipient(s); wherein the said layer provides a immediate or fast release of active principle(s); and b) at least one layer comprising another or same active principle(s) wherein layer (b) provides residence time of the dosage form in the gastrointestinal tract.

Another object of the invention is to provide a novel pharmaceutical composition in the form of a multilayer tablet comprising, a) at least one layer which comprises, a therapeutically effective amount of active principle(s) or a pharmaceutically acceptable salt or enantiomer or polymorph thereof, pharmaceutically acceptable excipient(s); wherein the said layer provides controlled release of active principle(s); and b) at least one layer comprising another or same active principle(s) wherein layer (b) provides increased residence time of the dosage form in the gastrointestinal tract.

Another object of the invention is to provide a novel pharmaceutical composition in the form of a multilayer tablet comprising, a) at least one layer which comprises, a therapeutically effective amount of active principle(s) or a pharmaceutically acceptable salt or enantiomer or polymorph thereof, pharmaceutically acceptable excipient(s); wherein the said layer provides a immediate or fast release of active principle(s); and b) at least one layer comprising another or same active principle(s) wherein layer (b) provides controlled and/or increased residence time of the dosage form in the gastrointestinal tract.

Yet another object of the invention is to provide a novel pharmaceutical composition comprising a therapeutically effective amount of active principle(s) or a pharmaceutically acceptable salt or enantiomer or polymorph thereof, optionally one or more release controlling agent(s) and pharmaceutical acceptable excipient(s) thereof, wherein the composition is formulated to increase the residence time of the said pharmaceutical composition and/or active principle(s) in the gastrointestinal tract, having an adhesive strength, measured as a force of detachment, of at least 100 mN when measured using advanced force gauge equipment (manufactured by Mecmesin, West Sussex, England).

DETAILED DESCRIPTION OF THE INVENTION

The present invention relates to a novel pharmaceutical composition, which comprises a therapeutically effective amount of active principle(s) or a pharmaceutically acceptable salt or enantiomer or polymorph thereof, optionally one or more controlled release agent(s) and pharmaceutical acceptable excipient(s) thereof, wherein the composition is formulated to increase the residence time of the said pharmaceutical composition and/or active principle(s) in the gastrointestinal tract. The pharmaceutical composition according to the invention can remain attached for desired period of time to the epithelial surface or to the mucosal membrane of the gastrointestinal tract. Since many drug compounds are absorbed exclusively in the small intestine or in a limited segment of the GI tract, it would therefore be beneficial to develop dosage forms such as sustained release dosage forms, which remains in the stomach and/or in the proximal and/or in the distal portion of the intestine for an extended period of time. The compositions of the present invention are preferably administered as once-a day. It can be administered twice a day or once a week.

Preferred group of drugs that could benefit from retained and controlled or immediate release in the gastrointestinal tract are those meant for the treatment of pathologies located in the stomach, the duodenum or the small intestine or colon.

The terms "active principle," "drug" "active agent" "active" and "pharmacologically active agent" are used interchangeably herein to refer to a chemical material or compound which, when administered to an organism (human or animal, generally human) induces a desired pharmacologic effect. In the context of the present invention the active principles are selected from the group comprising anti-infectives, penicillins, cephalosporins, cyclines, beta-lactamase inhibitors, aminosides, quinolones, nitroimidazoles, sulfamides, antihistaminics, antiallergics, anesthetics, steroidal or non-steroidal anti-inflammatories, analgesics with local or systemic effect, antispasmodics, anticancers, diuretics, beta-blockers, antihypertensives, antianginals, antiarrhythmics, vasodilators, bradycardic agents, calcium inhibitors, sedatives, cardiotonics, antifungals, antiulceratives, vasotonics, vasoprotectants, anti-ischemics, antiemetics, anticoagulants, antithrombotics, immunosuppressants, immunomodulators, antivirals, antiretrovirals, antidiabetics, hypolipidemics, agents for combating obesity, anticonvulsants, hypnotics, antiparkinsonians, antimigraines, neuroleptics, anxiolytics, antidepressants, psychostimulants, agents for promoting memory, bronchodilators, antitussives, agents for combating osteoporosis, peptides, hormones, steroids, enzymes, enzyme inhibitors, proteins, melatonergic agonists or antagonists, hormonal agents, acidity reducing agents (e.g., buffering agents such as potassium phosphate dibasic, calcium carbonate, sodium bicarbonate, sodium and potassium hydroxide, etc.) or combinations thereof.

The preferred active agents that can be used in conjunction with the present invention include rifaximin, vancomycin, mesalamine, cholestesamine, balasalazide, sulfasalazine etc.

"Therapeutically effective amount" means that the amount of active agent, which halts or reduces the progress of the condition being treated or which otherwise completely or partly cures or acts palliatively on the condition. A person skilled in the art can easily determine such an amount by routine experimentation and with an undue burden.

"Controlled release," means drug delivery system releasing the drug at a predetermined rate, locally or systemically, for a specified period of time. Controlled release can be used interchangeably with prolonged release, programmed release, timed release, extended release, sustained release and other such dosage forms.

"Optional" or "optionally" means that the subsequently described circumstance may or may not occur, so that the description includes instances where the circumstance occurs and instances where it does not.

By "pharmaceutically acceptable" is meant a carrier comprised of a material that is not biologically or otherwise undesirable.

"Entities" or "Entity" can be interchangeably used with granules, pellets, beads, minitablets and the like.

In an embodiment prolonged gastrointestinal residence can be obtained by using oral mucoadhesive formulation and/or by reducing gastrointestinal motility or a combination of one or more techniques.

In another embodiment, the gastroretentivity of the dosage form composition might also be achieved by delaying the gastric emptying time such as by administration of food.

The term "mucoadhesive" can be used interchangeably with "bioadhesive" and is defined as a natural or synthetic component, including macromolecules, polymers, and oligomers, or mixtures thereof, that can adhere to a subject's mucous membrane.

"Bioadhesion" or "mucoadhesion" is defined as the ability of a material to adhere to a biological tissue for an extended period of time. Bioadhesion is one solution to the problem of inadequate residence time resulting from stomach emptying and intestinal peristalsis, and from displacement by ciliary movement. For sufficient bioadhesion to occur, an intimate contact must exist between the bioadhesive and the receptor tissue, the bioadhesive must penetrate into the crevice of the tissue surface and/or mucus, and mechanical, electrostatic, or chemical bonds must form. Bioadhesive properties of polymers are affected by both the nature of the polymer and by the nature of the surrounding media.

"Residence time" is the time required for a pharmaceutical dosage form to transit through the stomach to the rectum i.e. the pharmaceutical dosage forms of the invention may have an increased retention time in the stomach and/or small and/or large intestine, or in the area of the gastrointestinal tract that absorbs the drug contained in the pharmaceutical dosage form. For example, pharmaceutical dosage forms of the invention can be retained in the small intestine (or one or two portions thereof, selected from the duodenum, the jejunum and the ileum). These pharmaceutical dosage forms as a whole, may include a bioadhesive polymeric coating that is applied to at least one surface of the dosage form.

Examples of mucoadhesives for use in the embodiments disclosed herein include, but are not limited to, natural, semi-synthetic and synthetic polymers.

Natural polymers include proteins (e.g., hydrophilic proteins), such as pectine, zein, modified zein, casein, gelatin, gluten, serum albumin, or collagen, chitosan, oligosaccharides and polysaccharides such as cellulose, dextrans, tamarind seed polysaccharide, gellan, carrageenan, xanthan gum, gum Arabic; hyaluronic acid, polyhyaluronic acid, alginic acid, sodium alginate.

When the bioadhesive polymer is a synthetic polymer, the synthetic polymer is typically selected from polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes, polystyrene, polymers of acrylic and methacrylic esters, polylactides, poly(butyric acid), poly(valeric acid), poly(lactide-co-glycolide), polyanhydrides, polyorthoesters, poly(fumaric acid), poly(maleic acid), and blends and copolymers or mixtures thereof.

Other polymers suitable for use in the invention include, but are not limited to, methyl cellulose, ethyl cellulose, hydroxypropyl cellulose, hydroxypropylmethyl cellulose, hydroxybutylmethyl cellulose, cellulose acetate, cellulose propionate, cellulose acetate butyrate, cellulose acetate phthalate, carboxymethyl cellulose, cellulose triacetate, cellulose sulfate sodium salt, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly(ethylene terephthalate), polyvinyl acetate), polyvinyl chloride, polystyrene, polyvinyl pyrrolidone, and polyvinylphenol. Polylactides, polyglycolides and copolymers thereof, poly(ethylene terephthalate), poly(butyric acid), poly(valeric acid), poly(lactide-co-caprolactone), poly[lactide-co-glycolide], polyanhydrides (e.g., poly(adipic anhydride)), polyorthoesters, blends and copolymers thereof.

Another group of polymers suitable for use as bioadhesive polymers are polymers having a hydrophobic backbone with at least one hydrophobic group pendant from the backbone. Suitable hydrophobic groups are groups that are generally non-polar. Examples of such hydrophobic groups include alkyl, alkenyl and alkynyl groups. Preferably, the hydrophobic groups are selected to not interfere and instead to enhance the bioadhesiveness of the polymers.

A further group of polymers suitable for use as bioadhesive polymers are polymers having a hydrophobic backbone with at least one hydrophilic group pendant from the backbone. Suitable hydrophilic groups include groups that are capable of hydrogen bonding or electrostatically bonding to another functional group. Example of such hydrophilic groups include negatively charged groups such as carboxylic acids, sulfonic acids and phosphonic acids, positively charged groups such as (protonated) amines and neutral, polar groups such as amides and imines.

Preferably, the hydrophilic groups are selected to not interfere and instead to enhance the bioadhesiveness of the polymers. In embodiments of the present invention, a pharmaceutical composition comprises an active agent and at least one swellable polymer.

Swellable polymers include, but are not limited to, a crosslinked poly(acrylic acid), a poly(alkylene oxide), a poly-vinyl alcohol), a polyvinyl pyrrolidone); a polyurethane hydrogel, a maleic anhydride polymer, such as a maleic anhydride copolymer, a cellulose polymer, a polysaccharide, starch, and starch based polymers.

Polymers can be modified by increasing the number of carboxylic groups accessible during biodegradation, or on the polymer surface. The polymers can also be modified by binding amino groups to the polymer. The polymers can be modified using any of a number of different coupling chemistries available in the art to covalently attach ligand molecules with bioadhesive properties to the surface-exposed molecules of the polymeric microspheres.

Lectins can be covalently attached to polymers to render them target specific to the mucin and mucosal cell layer. The attachment of any positively charged ligand, such as polyethyleneimine or polylysine, to a polymer may improve bioadhesion due to the electrostatic attraction of the cationic groups coating the beads to the net negative charge of the mucus. The mucopolysaccharides and mucoproteins of the mucin layer, especially the sialic acid residues, are responsible for the negative charge coating. Any ligand with a high binding affinity for mucin could also be covalently linked to most polymers with the appropriate chemistry, such as with carbodiimidazole (CDI), and be expected to influence the binding to the gut. For example, polyclonal antibodies raised against components of mucin or else intact mucin, when covalently coupled to a polymer, would provide for increased bioadhesion. Similarly, antibodies directed against specific cell surface receptors exposed on the lumenal surface of the intestinal tract would increase the residence time when coupled to polymers using the appropriate chemistry. The ligand affinity need not be based only on electrostatic charge, but other useful physical parameters such as solubility in mucin or specific affinity to carbohydrate groups.

The covalent attachment of any of the natural components of mucin in either pure or partially purified form to the polymers generally increases the solubility of the polymer in the mucin layer. The list of useful ligands include but are not limited to the following: sialic acid, neuraminic acid, n-acetyl-neuraminic acid, n-glycolylneuraminic acid, 4-acetyl-n-acetylneuraminic acid, diacetyl-n-acetyl-neuraminic acid, glucuronic acid, iduronic acid, galactose, glucose, mannose, fucose, any of the partially purified fractions prepared by chemical treatment of naturally occurring mucin, e.g., mucoproteins, mucopolysaccharides and mucopolysaccharide-protein complexes, and antibodies immunoreactive against proteins or sugar structure on the mucosal surface.

The attachment of polyamino acids containing extra pendant carboxylic acid side groups, such as polyaspartic acid and polyglutamic acid, may also increase bioadhesiveness. The polyamino chains would increase bioadhesion by means of chain entanglement in mucin strands as well as by increased carboxylic charge.

A bioadhesive controlled release pharmaceutical dosage form of the invention can have one or more coatings such as enteric coating, controlled release coating, film coating, sugar coating, bioadhesive coating. In one example, the additional coating prevents the bioadhesive dosage form from contacting the mouth or esophagus. In another example, the coating remains intact until reaching the small intestine (e.g., an enteric coating). Examples of coatings include methyl-methacrylates, zein, cellulose acetate, cellulose phthalate, HMPC, sugars, enteric polymers, gelatin and shellac. Premature exposure of a bioadhesive layer or dissolution of a pharmaceutical dosage form in the mouth can be prevented with a layer or coating of hydrophilic polymers such as HPMC or gelatin.

Coating agents which are useful in the coating process, include, but are not limited to, polysaccharides such as maltodextrin, alkyl celluloses such as methyl or ethyl cellulose, hydroxyalkylcelluloses (e.g. hydroxypropylcellulose or hydroxypropylmethylcelluloses); polyvinylpyrrolidone, acacia, corn, sucrose, gelatin, shellac, cellulose acetate pthalate, lipids, synthetic resins, acrylic polymers, opadry, polyvinyl alcohol, copolymers of vinylpyrrolidone and vinyl acetate (e.g. marketed under the brand name of Plasdone) and polymers based on methacrylic acid such as those marketed under the brand name of Eudragit. These may be applied from aqueous or non-aqueous systems or combinations of aqueous and non-aqueous systems as appropriate.

The bioadhesive polymers discussed above can be mixed with one or more plasticizers or thermoplastic polymers. Such agents typically increase the strength and/or reduce the brittleness of polymeric coatings. The plasticizers include dibutyl sebacate, polyethylene glycol, triethyl citrate, dibutyl adipate, dibutyl fumarate, diethyl phthalate, ethylene oxide-propylene oxide block copolymers and di(sec-butyl) fumarate, thermoplastic polymers include polyesters, poly(caprolactone), polylactide, poly(lactide-co-glycolide), methyl methacrylate, cellulose and derivatives thereof such as ethyl cellulose, cellulose acetate and hydroxypropyl methyl cellulose and large molecular weight polyanhydrides. Antitacking agents such as talc, stearic acid, magnesium stearate and colloidal silicon dioxide and the like. Surfactants such as polysorbates and sodium lauryl sulphate and opacifying agents such as titanium dioxide and the like. All these excipients can be used at levels well known to the persons skilled in the art.

A pharmaceutical dosage form can have one or more coatings in addition to the bioadhesive polymeric coating, e.g., covering the surface of the bioadhesive coating. These coatings and their thickness can, for example, be used to control where in the gastrointestinal tract the bioadhesive coating becomes exposed.

Pharmaceutical dosage forms of the invention can be coated by a wide variety of methods. Suitable methods include compression coating, coating in a fluidized bed or a pan and hot melt (extrusion) coating. Such methods are well known to those skilled in the art.

Also suitable are rupturable coating systems, e.g., Pulsincap, that use osmotic forces of swelling from hydrophilic polymers to rupture enteric membranes to reveal underlying bioadhesive dosage form.

Alternately, non-permeable coatings of insoluble polymers, e.g., cellulose acetate, ethylcellulose, can be used as enteric coatings for delayed/modified release (DR/MR) by inclusion of soluble pore formers in the coating, e.g., PEG, PVA, sugars, salts, detergents, triethyl citrate, triacetin, etc.

Also, coatings of polymers that are susceptible to enzymatic cleavage by colonic bacteria are another means of ensuring release to distal ileum and ascending colon. Materials such as calcium pectinate can be applied as coatings to tablets and multiparticulates and disintegrate in the lower gastrointestinal tract, due to bacterial action. Calcium pectinate capsules for encapsulation of bioadhesive multiparticulates are also available.

The pharmaceutically acceptable excipients, are selected from the group comprising binders, diluents, lubricants, surfactants and glidants.

Binder is one or more selected from the group comprising carbohydrates like celluloses their derivatives; starches; gums; polyvinylpyrrolidone, povidone, syrup, polyethylene oxide, polyacryl amide, poly-N-vinyl amide, sodium carboxymethyl cellulose, polyethylene glycol, gelatin, polyethylene oxide, poly propylene glycol, tragacanth, alginic acid, combinations thereof.

Diluent is one or more selected from the group comprising carbohydrates, derivatives of carbohydrates, polyols, sugar alcohols, carbonate, sulphate or phosphate salts of inorganic metals or mixtures thereof.

Lubricants is one or more selected from the group comprising Magnesium, Aluminium, Zinc or Calcium stearate, polyethylene glycol, mineral oil, sodium stearyl fumarate, stearic acid, hydrogenated vegetable oil, glyceryl behenate, glyceryl palmitostearate, glyceryl stearate, cornstarch, talc, calcium silicate, magnesium silicate, colloidal silicon dioxide, silicon hydrogel, and mixtures thereof.

Surfactant can be selected from ionic or non-ionic or zwitterionic surfactants.

Glidant is one or more selected from the group comprising silicon dioxide, colloidal silica, powdered cellulose, talc, tribasic calcium phosphate and mixtures thereof.

The novel pharmaceutical composition of the present invention can further have solubilizing agents. Solubilizing agents include but are not limited to surfactants, cyclodextrin and its derivatives, lipophilic substances or any combination thereof.

Unlimiting examples of surfactants include water-soluble or water dispersible nonionic, semi-polar nonionic, anionic, cationic, amphoteric, or zwitterionic surface-active agents; or any combination thereof.

Other solubilizing agents include vitamin E and its derivatives; monohydric alcohol esters such as trialkyl citrates, lactones and lower alcohol fatty acid esters; nitrogen-containing solvents; phospholipids; glycerol acetates such as acetin, diacetin and triacetin; glycerol fatty acid esters such as mono-, di- and triglycerides and acetylated mono- and diglycerides; propylene glycol esters; ethylene glycol esters; and combinations thereof.

In another embodiment of the novel pharmaceutical composition of the present invention can further have stabilizing agents. Stabilizing agents include but are not limited to catalysts, antioxidants, adsorbents, absorbents, buffers, chelating and sequestering agents, carbonate salt of said amino acid is present as either the group I or II alkali or alkali earth metal salt and combinations thereof.

Pharmaceutical compositions of the invention is but not limited to powders, pellets, beads, granules, tablets, compacts, sustained release formulations, capsules, microcapsules, tablets in capsules, tablets in tablets, microspheres, shear form particles, floss, and flakes or mixtures thereof. Tablets include single layered tablets, multilayered tablets, mini tablets, bioadhesive tablets, caplets, matrix tablets, tablet within a tablet, mucoadhesive tablets. Sustained release is formulation include but are not limited to matrix type controlled release, membrane diffusion controlled release, site targeted, osmotically controlled release, pH dependent delayed release, timed release, pulsatile release, hydrodynamic balanced system; powders, pellets, beads, granules for suspension.

Multi-layer tablets comprises a first, a second or/and a third layer, where each layer includes one or more excipients and optionally one or more drug.

At least one layer of the tablet includes a hydrophobic excipient or hydrophilic excipient or combinations thereof.

Exemplary hydrophobic excipients include celluloses, particularly cellulose acetate and ethyl cellulose, stearic acid, magnesium stearate, glycerol monostearate, fatty acids and salts thereof, monoglycerides, diglycerides, triglycerides, oil, colloidal silicon dioxide and talc.

Such tablets include one excipient present in an amount sufficient to be at least partially rate-controlling with respect to release of the drug from the tablet.

For tablets containing two or more drugs, the drugs can both be present in one or more layers or the different drugs are present in separate layers.

For drugs requiring absorption in the stomach and upper small intestine and/or topical delivery to these sites, particularly drugs with narrow absorption windows, bioadhesive, gastroretentive drug delivery systems are the option of choice. Drugs requiring absorption or topical delivery only in the small intestine, enteric-coated, bioadhesive drug delivery systems are preferred. For drugs requiring absorption or topical delivery only in the lower small intestine and colon enteric-coated, bioadhesive drug delivery systems are preferred.

Multi-layer or gradient tablets can be assembled in several different ways.

In one embodiment, the tablet comprises at least one controlled release layer and one bioadhesive layer, where in controlled release layer comprises one or more pharmaceutical polymers and/or pharmaceutical excipients, one or more drugs.

In one embodiment, the tablet comprises at least one controlled release layer and one bioadhesive layer, each comprising one or more pharmaceutical polymers and/or pharmaceutical excipients, optionally one or more drugs. Such tablets can also be used to commence release of different drugs at different times, by inclusion of different drugs in separate layers.

In one embodiment, the tablet comprises at least one solid inner layer and two solid outer layers, each comprising one or more pharmaceutical polymers and/or pharmaceutical excipients. The inner layer comprises one or more active ingredient and rate-controlling polymer. The two solid outer layers are bioadhesive.

In one embodiment, the tablet comprises at least one solid inner layer and two solid outer layers, each comprising one or more drugs and one or more pharmaceutical polymers and/or pharmaceutical excipients. Such tablets can also be used to commence release of different drugs at different times, by inclusion of different drugs in separate layers.

In another embodiment, the multi-layer tablet consists of a solid inner layer and two solid outer layers, each comprising a drug and one or more pharmaceutical polymers or pharmaceutical excipients, wherein at least one polymer or excipient is hydrophobic.

In an embodiment, the composition of the present invention comprises at least two fractions wherein one fraction is an immediate release or fast release fraction providing an immediate release of the active agent and the other fraction is an extended release fraction that releases the active agent over extended periods of time.

One or more layers of the tablet can contain permeation enhancers to provide permeability enhancement of drugs through mucosal lining of the gastrointestinal tract (GIT). An absorption enhancer facilitates the uptake of a drug across the gastrointestinal epithelium. Absorption enhancers include compounds that improve the ability of a drug to be solubilized in the aqueous environment in which it is originally released and/or in the lipophilic environment of the mucous layer lining of the intestinal walls.

In still another embodiment, the multi-layer tablet is enteric coated. Optionally Eudragit FS 30D or other suitable polymer may be incorporated in coating composition to retard the release of the drug to ensure drug release in the colon.

It is also an object of the invention to provide the a pharmaceutical composition, wherein the said composition is formulated by compressing or compacting powder, granules, pellets, beads, shear form particles, floss, or the like, or combinations thereof. The said composition of the present invention may be filled into capsule or made into a capsule, wherein the said capsule is in the form of a hard gelatin capsule or soft gelatin capsule.

It is also an object of the present invention to provide pharmaceutical composition wherein the composition is in the form of a compressed or compacted multiparticulate composition comprising a blend of one or more types of particles, granules, pellets, beads, compacts, minitablets, shear form particles, floss, or the like, or combinations thereof, having different release characteristics or a multiparticulate composition made into a capsule or filled into a capsule.

It is also an object of the present invention to provide a pharmaceutical composition of active principle(s), wherein the composition is in the sustained release form, timed release form, pulsatile release form, prolonged release form, extended release form or delayed release form, or a combination thereof. The composition can also additionally comprise an immediate release composition.

The compositions can be prepared in an easy and cost effective manner.

The foregoing examples are illustrative embodiments of the invention and are merely exemplary. A person skilled in the art may make variations and modifications without deviating from the spirit and scope of the invention. All such modifications and variations are intended to be included within the scope of the invention.

EXAMPLES

Example 1

| Ingredients | % w/w |
| --- | --- |
| Active | 20 |
| Sodium Alginate | 40 |
| Water | QS |
| Calcium chloride | 15 |
| Polyethylene oxide (PEO) | 10 |
| Sodium Carboxymethyl Cellulose (NaCMC) | 11 |
| Colloidal silicon dioxide | 2 |
| Magnesium stearate | 2 |

Procedure
i) Sodium alginate is suspended in water and active was suspended in this colloidal solution.
ii) Calcium Chloride is dissolved in water and kept aside.
iii) Add step (i) into step (ii) dropwise to make beads under stirring, further filter the solution to separate the beads and dry the beads.
iv) Mix the dried beads with xanthan gum and sodium alginate.
v) Lubricate the beads of step (iv) with magnesium stearate and fill into capsules or sachets or filled in bottles with sweetening and flavouring agents as a powder for suspension.

Example 2

| Ingredients | % w/w |
| --- | --- |
| Active | 25 |
| Diluents (e.g., Mannitol or DCP or MCC) | 40 |
| PEO | 20 |
| Polyvinyl Pyrolidone (PVP) | 10 |
| Isopropyl Alcohol (IPA) | QS |
| Magnesium Stearate | 2 |
| Colloidal silicon dioxide | 2 |

Procedure:
i) Sift Active, Diluent, PVP and PEO through a suitable seive.
ii) Granulate blend of step (i) with IPA.
iii) Dry the granules of step (ii) and sift through a suitable seive.
iv) Lubricate the granules of step (iii) with magnesium stearate.
v) The bioadhesive granules of step (iv) can be further compressed into tablets using suitable diluents and lubricants or filled into capsules or sachets or filled into bottle with sweetening and flavouring agents as a powder for suspension.

Example 3

| Ingredients | % w/w |
| --- | --- |
| Active | 20 |
| Diluent (MCC/DCP) | 40 |
| Sodium Alginate | 10 |
| Xanthan gum | 10 |
| NaCMC | 15 |
| Sodium bicarbonate | 4 |
| Sodium Lauryl Sulphate (SLS) | 1 |
| Water | QS |

Procedure:
Spheronization
i) Mix all the ingredients except sodium bicarbonate in a blender.
ii) Dissolve sodium bicarbonate in water.
iii) Granulate (ii) with (i)
iv) Wet mass of step (ii) is passed through Extruder and further spheronized to get the round pellets
The pellets can be filled into capsules, sachets or filled in bottles with sweetening and flavouring agents as a powder for suspension or compressed into tablets.

Example 4

| Ingredients | % w/w |
| --- | --- |
| Active | 30 |
| Diluents (e.g., Mannitol or DCP or MCC) | 30 |
| HPMC | 10 |
| Poloxamer | 10 |
| PEO | 10 |
| Colloidal silicon dioxide | 5 |
| Magnesium stearate | 5 |

Procedure:
i) Sift Active, Diluent, HPMC, Poloxamer and PEO through a suitable seive
ii) dry blend (i) in a blender.
iii) sift colloidal silicon dioxide and magnesium stearate through a suitable seive.
iv) Lubricate (ii) with (iii) in a blender.
v) The blend is then compressed into tablets

Example 5

| Ingredients | % W/W |
| --- | --- |
| Active | 30 |
| Diluents (e.g. Mannitol or DCP or MCC) | 30 |
| HPMC | 10 |
| Poloxamer | 10 |
| Sodium Alginate | 10 |
| Colloidal silicon dioxide | 5 |
| Magnesium Stearate | 5 |

Procedure:
i) Active, Diluents, HPMC, Poloxamer and sodium alginate are sifted through a suitable seive.
ii) Step (i) is dry blended in a blender.
iii) Lubricants are sifted through a suitable seive and mixed with step (ii).
iv) Blend of step (iii) is then compressed into mini tablets.
v) These mini tablets can be filled into capsules

Example 6

B) First and Third Layer

| Ingredients | % W/W |
| --- | --- |
| Active | 5 |
| HPMC | 35 |
| PEO | 40 |
| Polycarbophil | 15 |
| Collodial Silicon Dioxide | 3 |
| Magnesium Stearate | 2 |

Procedure:
i) Sift active, HPMC, PEO and Polycarbophil through a suitable seive.
ii) dry blend (i) in a blender.
iii) sift colloidal silicon dioxide and magnesium stearate through a suitable seive.
iv) Lubricate (ii) with (iii) in a blender.
v) Divide (iv) into equal portions for first and third layer.

A) Middle Layer

| Ingredients | % W/W |
|---|---|
| Active | 70 |
| Diluents (E.g., Mannitol or DCP or MCC) | 16 |
| HPMC | 10 |
| Colloidal silicon dioxide | 2 |
| Magnesium Stearate | 2 |

Procedure
i) Sift active, diluent and HPMC through a suitable seive
ii) dry blend (i) in an blender/granulation can be done using IPA or water.
iii) sift colloidal silicon dioxide and magnesium stearate through a suitable seive.
iv) Lubricate (ii) with (iii) in a blender.
Blends of A and B are compressed into trilayer tablets Example 7

| Ingredients | % W/W |
|---|---|
| Active | 20 |
| Diluents (e.g. Mannitol or DCP or MCC) | 25 |
| HPMC | 10 |
| PEO | 15 |
| Vitamin E TPGS* | 20 |
| Colloidal silicon dioxide | 3 |
| Magnesium Stearate | 2 |

*D-alpha-tocopheryl polyethylene glycol 1000 succinate

Procedure
i) Mix active with Vitamin E TGPS at 70° C., cool to room temperature.
ii) Pulverize (i) using a suitable sieve
iii) Mix (ii) with all other excipients except the lubricants in a blender.
iv) Mix (iii) with magnesium stearate and colloidal silicon dioxide in a blender.
v) The blend is then compressed into tablets.

Example 8

B) First and Third Layer

| Ingredients | % W/W |
|---|---|
| Active | 5 |
| HPMC | 30 |
| PEO | 40 |
| Polyvinyl alcohol (PVA) | 10 |
| SLS | 10 |
| Collodial Silicon Dioxide | 3 |
| Magnesium Stearate | 2 |

Procedure:
i) Sift active, HPMC, PEO, PVA and SLS through a suitable seive.
ii) dry blend (i) in a blender.
iii) sift colloidal silicon dioxide and magnesium stearate through a suitable seive.
iv) Lubricate (ii) with (iii) in a blender.
v) Divide (iv) into equal portions for first and third layer.

A) Middle layer

| Ingredients | % W/W |
|---|---|
| Active | 70 |
| Diluents (E.g., Mannitol or DCP or MCC) | 15 |
| HPMC | 10 |
| Colloidal silicon dioxide | 3 |
| Magnesium Stearate | 2 |

Procedure
i) Sift active, diluent and HPMC through a suitable seive
ii) dry blend (i) in a blender/granulation can be done using IPA or water.
iii) sift colloidal silicon dioxide and magnesium stearate through a suitable seive.
iv) Lubricate (ii) with (iii) in a blender.
Blends of A and B are compressed into trilayer tablets Example 9

| Ingredients | % w/w |
|---|---|
| Active | 30 |
| Dliuents (e.g., Mannitol or DCP or MCC) | 30 |
| HPMC | 15 |
| PEO | 25 |
| Colloidal silicon dioxide | 3 |
| Magnesium stearate | 2 |
| Methylene chloride | QS |
| IPA | QS |

Procedure:
i) Sift Active, Diluent, HPMC and PEO through a suitable seive.
ii) dry blend (i) in a blender.
iii) Granulate (ii) with IPA:Methylene chloride.
iv) Dry (iii) in fluid bed dryer.
v) Granules obtained in (iv) are sifted through a suitable seive.
vi) Sift Colloidal silicon dioxide and magnesium stearate through suitable seive
vii) Lubricate (v) with (vi) in a blender.
v) The blend is then compressed into tablets Example 10

| Ingredients | % w/w |
|---|---|
| Active | 40 |
| Dliuents (e.g., Mannitol or DCP or MCC) | 10 |
| HPMC | 20 |
| PEO | 20 |
| NaCMC | 5 |
| Colloidal silicon dioxide | 3 |
| Magnesium stearate | 2 |

Procedure
i) Sift Active, Diluent, HPMC, NaCMC and PEO through a suitable seive
ii) dry blend (i) in a blender.

iii) Sift Colloidal silicon dioxide and magnesium stearate through a suiatble seive
iv) Add half quantity of (iii) to (ii) and mix in a blender.
v) Compact blend of (iv) using a roller compactor at a pressure.
vi) sift (v) through suitable seive to obtain granules
vii) Mix remaining quantity of (iii) and (vi) in a blender.
viii) Blend of (vii) is compressed into tablets.

Example 11

| Ingredients | % w/w |
| --- | --- |
| Active | 50 |
| Dliuents (e.g., Mannitol or DCP or MCC) | 15 |
| HPMC | 10 |
| PEO | 15 |
| Guar gum | 5 |
| Colloidal silicon dioxide | 3 |
| Magnesium stearate | 2 |
| Water | QS |

Procedure:
i) Sift active, diluent, HPMC, guar gum and PEO through a suitable seive
ii) dry blend (i) in a blender.
iii) Granulate (ii) with water and dry the wet mass in fluid bed dryer.
iv) Granules obtained in (iii) are sifted through a suitable seive.
v) Sift Colloidal silicon dioxide and magnesium stearate through a suitable seive.
vi) Lubricate (iv) with (v).
vii) Blend of step (vi) is then compressed into tablets.

Example 12

A) First Layer

| Ingredients | % w/w |
| --- | --- |
| Active | 40 |
| Dliuents (e.g., Mannitol or DCP or MCC) | 25 |
| HPMC | 30 |
| Colloidal silicon dioxide | 3 |
| Magnesium stearate | 2 |
| IPA | QS |
| Methylene chloride | QS | i) Sift active, diluent and HPMC through a suitable sieve and mix in a blender.
iii) Granulate (i) with IPA:methylene chloride, and dry the wet mass in a fluid bed dryer.
iii) Granules of (iii) passed through a suitable sieve.
iv) Sift colloidal silicon dioxide and magnesium stearate through a suitable seive
v) Lubricate (iv) with (v).
B) Second layer

| Ingredients | % w/w |
| --- | --- |
| HPMC | 30 |
| PEO | 35 |
| Dliuents (e.g., Mannitol or DCP or MCC) | 25 |
| Colloidal silicon dioxide | 5 |
| Magnesium stearate | 5 | i) Sift HPMC, diluent and PEO through a suitable seive.
ii) dry blend (i) in a blender.
iii) sift colloidal silicon dioxide and magnesium stearate through a suitable seive.
iv) Lubricate (ii) with (iii) in a blender.
Compress both A and B to form bilayer tablet.

Example 13

B) First and Third Layer

| Ingredients | % W/W |
| --- | --- |
| HPMC | 40 |
| Xanthan gum | 20 |
| Polycarbophil | 25 |
| Colloidal silicon dioxide | 5 |
| Magnesium stearate | 5 |

Procedure:
i) Sift HPMC, Xanthan gum and Polycarbophil through a suitable seive.
ii) dry blend (i) in a blender.
iii) sift colloidal silicon dioxide and magnesium stearate through a suitable seive.
iv) Lubricate (ii) with (iii) in a blender.
A) Middle layer

| Ingredients | % W/W |
| --- | --- |
| Active | 50 |
| Diluents (e.g., Mannitol or DCP or MCC) | 15 |
| HPMC | 10 |
| Colloidal silicon dioxide | 7 |
| Magnesium stearate | 3 |
| Water | QS | i) Sift active, diluent, and HPMC through a suitable selve
ii) dry blend (i) in a blender.
iii) Granulate (i) with (ii) and dry the wet mass in fluid bed dryer
iv) Granules obtained in (iii) are sifted through a suitable seive.
v) Sift Colloidal silicon dioxide and magnesium stearate through a suitable seive.
vi) Lubricate (iv) with (v).
vii) Blend of A and B is then compressed into trilayered tablet.

Example 14

B) First and Third Layer

| Ingredients | % W/W |
| --- | --- |
| HPMC | 40 |
| Xanthan gum | 20 |
| PEO | 30 |
| Colloidal silicon dioxide | 5 |
| Magnesium stearate | 5 |

Procedure:
i) Sift HPMC, Xanthan gum and PEO through a suiatble seive
ii) dry blend (i) in a blender.
iii) sift colloidal silicon dioxide and magnesium stearate through a suitable seive.
iv) Lubricate (ii) with (iii) in a blender.

A) Middle Layer

| Ingredients | % W/W |
| --- | --- |
| Active | 40 |
| Diluents (e.g., Mannitol or DCP or MCC) | 10 |
| HPMC | 15 |
| Colloidal silicon dioxide | 3 |
| Magnesium stearate | 2 |
| IPA | QS |
| Methylene chloride | QS |

Procedure:
i) Sift active, diluent, and HPMC through a suitable seive.
ii) dry blend (i) in a blender.
iii) Granulate (ii) with IPA:methylene chloride and dry the wet mass in fluid bed dryer.
iv) Granules obtained in (iii) are sifted through a suitable seive.
v) Sift Colloidal silicon dioxide and magnesium stearate through a suitable seive.
vi) Lubricate (iv) with (v).
viii) Blend A and B are then compressed into trilayer tablet.

Example 15

A) First Layer

| Ingredients | % w/w |
| --- | --- |
| Active | 35 |
| HPMC | 15 |
| PEO | 20 |
| Dliuents (e.g., Mannitol or DCP or MCC) | 25 |
| Colloidal silicon dioxide | 2 |
| Magnesium stearate | 3 |
| Water | QS |

Procedure
i) Sift active, diluent, HPMC and PEO through a suitable sieve and mix in a blender.
ii) granulate (i) with water and dry the wet mass in a fluid bed dryer.
iii) granules of (ii) passed through a suitable sieve.
iv) sift colloidal silicon dioxide and magnesium stearate through a suitable seive
v) lubricate (iv) with (v).

B) Second Layer

| Ingredients | % w/w |
| --- | --- |
| HPMC | 40 |
| PEO | 35 |
| Carbomer | 15 |
| Colloidal silicon dioxide | 5 |
| Magnesium stearate | 5 | i) Sift HPMC, carbomer and PEO through a suitable seive
ii) dry blend (i) in a blender.
iii) sift colloidal silicon dioxide and magnesium stearate through a suitable seive.
iv) Lubricate (ii) with (iii) in a blender.
Blends of A and B are then compressed into bilayer tablets.

Example 16

A) First Layer

| Ingredients | % w/w |
| --- | --- |
| Active | 30 |
| HPMC | 30 |
| Xanthan gum | 10 |
| Dliuents (e.g., Mannitol or DCP or MCC) | 25 |
| Colloidal silicon dioxide | 3 |
| Magnesium stearate | 2 | i) Sift active, diluent, HPMC and xanthan gum through a suitable seive
ii) dry blend (i) in a blender.
iii) sift colloidal silicon dioxide and magnesium stearate through a suitable seive.
iv) Lubricate (ii) with (iii) in a blender.

B) Second Layer

| Ingredients | % w/w |
| --- | --- |
| HPMC | 35 |
| PEO | 35 |
| Diluents (e.g., Mannitol or DCP or MCC) | 20 |
| Colloidal silicon dioxide | 5 |
| Magnesium stearate | 5 | i) Sift HPMC, diluent and PEO through a suitable seive
ii) dry blend (i) in a blender.
iii) sift colloidal silicon dioxide and magnesium stearate through a suitable seive.
iv) Lubricate (ii) with (iii) in a blender.
Blends of A and B are then compressed into bilayer tablets.

Example 17

B) First and Third Layer

| Ingredients | % W/W |
| --- | --- |
| HPMC | 40 |
| Xanthan gum | 20 |
| Polycarbophil | 25 |
| Colloidal silicon dioxide | 5 |
| Magnesium stearate | 5 |

Procedure:
i) Sift HPMC, Xanthan gum and Polycarbophil through a suitable seive
ii) dry blend (i) in a blender.
iii) sift colloidal silicon dioxide and magnesium stearate through a suitable seive.
iv) Lubricate (ii) with (iii) in a blender.

A) Middle layer

| Ingredients | % W/W |
| --- | --- |
| Active | 40 |
| Diluents (e.g., Mannitol or DCP or MCC) | 20 |
| HPMC | 15 |
| PEO | 15 |
| Colloidal silicon dioxide | 7 |
| Magnesium stearate | 3 |
| Water | QS | i) Sift active, diluent, HPMC and PEO through a suitable seive.
ii) dry blend (i) in a blender.
iii) Granulate (ii) with water and dry the wet mass in fluid bed dryer.
iv) Granules obtained in (iii) are sifted through a suitable seive.
v) Sift Colloidal silicon dioxide and magnesium stearate through a suitable seive.
vi) Lubricate (iv) with (v).
vii) Blend of A and B is then compressed into trilayered tablets.

Example 18

A) First Layer

| Ingredients | % w/w |
|---|---|
| Active | 70 |
| HPMC | 5 |
| Diluents (e.g., Mannitol or DCP or MCC) | 21 |
| Colloidal silicon dioxide | 2 |
| Magnesium stearate | 2 |

Procedure:
i) Sift active, diluent, HPMC and diluent through a suitable seive.
ii) dry blend (i) in a blender.
iii) sift colloidal silicon dioxide and magnesium stearate through a suitable seive.
iv) Lubricate (ii) with (iii) in a blender.

B) Second Layer

| Ingredients | % w/w |
|---|---|
| Active | 40 |
| HPMC | 35 |
| Diluents (e.g., Mannitol or DCP or MCC) | 20 |
| Colloidal silicon dioxide | 3 |
| Magnesium stearate | 2 | i) Sift active, diluent, HPMC and diluent through a suitable seive.
ii) dry blend (i) in a blender.
iii) sift colloidal silicon dioxide and magnesium stearate through a suitable seive.
iv) Lubricate (ii) with (iii) in a blender.

C) Third Layer

| Ingredients | % w/w |
|---|---|
| HPMC | 40 |
| Xanthan gum | 20 |
| PEO | 30 |
| Colloidal silicon dioxide | 5 |
| Magnesium stearate | 5 | i) Sift xanthan gum, PEO and HPMC through a suitable seive.
ii) dry blend (i) in a blender.
iii) sift colloidal silicon dioxide and magnesium stearate through a suitable seive.
iv) Lubricate (ii) with (iii) in a blender.
Blend of A, B and C is then compressed into trilayered tablets.

Example 19

A) First Layer

| Ingredients | % w/w |
|---|---|
| Active | 50 |
| HPMC | 20 |
| Carbomer | 10 |
| Dliuents (e.g., Mannitol or DCP or MCC) | 15 |
| Colloidal silicon dioxide | 2 |
| Magnesium stearate | 3 |

Procedure:
i) Sift active, HPMC, carbomer and diluents through a suitable seive
ii) dry blend (i) in a blender.
iii) sift colloidal silicon dioxide and magnesium stearate through a suitable seive.
iv) Lubricate (ii) with (iii) in a blender.

B) Second Layer

| Ingredients | % w/w |
|---|---|
| HPMC | 30 |
| PEO | 40 |
| Xanthan gum | 20 |
| Colloidal silicon dioxide | 2 |
| Magnesium stearate | 3 | i) Sift HPMC, xanthan gum and PEO through a suitable seive
ii) dry blend (i) in a blender.
iii) sift colloidal silicon dioxide and magnesium stearate through a suitable seive.
iv) Lubricate (ii) with (iii) in a blender.
Blends of A and B are then compressed into bilayer tablets.

Example 20

| Ingredients | % W/W |
|---|---|
| Active | 2 |
| Diluents (e.g. Mannitol or DCP or MCC) | 15 |
| HPMC | 30 |
| PEO | 45 |
| Stabilizing agent | 5 |
| Colloidal silicon dioxide | 2 |
| Magnesium Stearate | 1 |

Procedure:
i) Active, Diluents, HPMC, stabilizing agent and PEO are sifted through a suitable seive.
ii) Step (i) is dry blended in a blender.
iii) Lubricants are sifted through a suitable seive and mixed with step (ii).
iv) Blend of step (iii) is then compressed into tablets.
HPMC=Hydroxy propyl methyl cellulose
PEO=Polyethyeleneoxide
DCP=Dicalcium phosphate
MCC=Microcrystalline cellulose
IPA=Iso Propyl alcohol
Determination of Bioadhesion
Bioadhesion was determined by tensiometric method. For the determination, an advanced force gauge equipment (mfg. by Mecmesin, West Sussex, England) was used. Freshly excised Sheep intestinal tissue was taken and stored in a Tyrode solution at 4° C. until used for the experiment. The tissue was cut into pieces (3×4 cm) and mounted on the glass slide and tightened with a thread. 0.5 ml Phosphate buffered saline (PBS) was placed on the tissue. The bioadhesive tablet prepared as in examples 1 to 6, was placed on this tissue and another 0.5 ml PBS was placed on the tablet. A glass slide with a 10 g weight was placed on the tablet and it was allowed to hydrate for 10 min., 30 min., 60 min., 840 and 960 min. At the specific time interval, the hydrated tablet along with slide was mounted on the stage of the bioadhesion apparatus. Probe was then lowered at fixed speed of 0.2 mm/sec. and upper slide was attached to the hook of the probe by means of a thread. The peak detachment force was considered as the bioadhesive force. The force required to separate the tablet from biological substrate was recorded in mN as demonstrated in accompanying FIG. 1.

Formula 1:

| Sr. No. | Ingredients | % w/w |
|---|---|---|
| 1. | PEO | 48.86 |
| 2. | MCC | 48.86 |
| 3. | colloidal silicon dioxide | 1.36 |
| 4. | Magnesium stearate | 0.91 | i) Sift MCC and PEO through a suitable seive.
ii) dry blend (i) in a blender.
iii) sift colloidal silicon dioxide and magnesium stearate through a suitable seive.
iv) Lubricate (ii) with (iii) in a blender.
   Compress into a tablet.

Formula 2:

| Sr. No. | Ingredients | % w/w |
|---|---|---|
| 1. | HPMC | 48.86 |
| 2. | MCC | 48.86 |
| 3. | Colloidal silicon dioxide | 1.36 |
| 5. | Magnesium stearate | 0.91 |

Formula 3:

| Sr. No. | Ingredients | % w/w |
|---|---|---|
| 1. | PEO | 48.86 |
| 2. | Xanthan gum | 48.86 |
| 3. | colloidal silicon dioxide | 1.36 |
| 5. | Magnesium stearate | 0.91 |

Formula 4:

| S. No. | Ingredients | % w/w |
|---|---|---|
| 1. | Xanthan Gum | 48.86 |
| 2. | MCC | 48.86 |
| 3. | Colloidal silicon dioxide | 1.36 |
| 4. | Magnesium Stearate | 0.91 |

Formula 5:

| S. No. | Ingredients | % w/w |
|---|---|---|
| 1. | PEO | 48.86 |
| 2. | Sodium CMC | 48.86 |
| 3. | Colloidal silicon dioxide | 1.36 |
| 4. | Magnesium Stearate | 0.91 |

Formula 6:

| S. No. | Ingredients | % w/w |
|---|---|---|
| 1. | Sodium CMC | 48.86 |
| 2. | MCC | 48.86 |
| 3. | Colloidal silicon dioxide | 1.36 |
| 4. | Magnesium Stearate | 0.91 |

All tablets are prepared as explained in Formula 1.

The invention claimed is:

1. An oral multilayer tablet comprising:
   a first layer comprising a pharmaceutical composition comprising rifaximin or a pharmaceutically acceptable salt thereof and that is configured for immediate or fast release of the rifaximin or salt thereof; and
   a second layer comprising the rifaximin or salt thereof and a polymer having affinity for gastrointestinal mucosa,
   wherein the polymer adheres to the gastrointestinal mucosa and provides increased residence time of the tablet in the gastrointestinal tract by bioadhesion which is independent of food effect,
   wherein the composition has an adhesive strength, measured as a force of detachment, of at least 1000 mN in 30 minutes, and
   wherein bioadhesion is provided for a period greater than 0.5 hour.

2. The multilayer tablet of claim 1, comprising at least one active principle in addition to rifaximin.

* * * * *